(12) United States Patent
Bulawa et al.

(10) Patent No.: US 12,268,669 B2
(45) Date of Patent: Apr. 8, 2025

(54) PHARMACEUTICAL COMPOSITIONS AND METHODS COMPRISING A COMBINATION OF A BENZOXAZOLE TRANSTHYRETIN STABILIZER AND AN ADDITIONAL THERAPEUTIC AGENT

(71) Applicant: Pfizer Inc., New York, NY (US)

(72) Inventors: Christine Ellen Bulawa, Arlington, MA (US); James Allan Fleming, Arlington, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/415,902

(22) PCT Filed: Dec. 17, 2019

(86) PCT No.: PCT/IB2019/060899
§ 371 (c)(1),
(2) Date: Jun. 18, 2021

(87) PCT Pub. No.: WO2020/128816
PCT Pub. Date: Jun. 25, 2020

(65) Prior Publication Data
US 2022/0071965 A1    Mar. 10, 2022

Related U.S. Application Data (60) Provisional application No. 62/782,403, filed on Dec. 20, 2018.

(51) Int. Cl.
| | |
|---|---|
| *A61K 31/423* | (2006.01) |
| *A61K 31/4025* | (2006.01) |
| *A61K 31/4245* | (2006.01) |
| *A61P 25/00* | (2006.01) |
| *C07K 16/18* | (2006.01) |
| *C12N 15/113* | (2010.01) |

(52) U.S. Cl.
CPC ........ *A61K 31/423* (2013.01); *A61K 31/4025* (2013.01); *A61K 31/4245* (2013.01); *A61P 25/00* (2018.01); *C07K 16/18* (2013.01); *C12N 15/113* (2013.01)

(58) Field of Classification Search
CPC .......................... A61K 31/423; A61K 31/4245
USPC .................................................. 514/364, 375
See application file for complete search history.

(56) References Cited

U.S. PATENT DOCUMENTS

| | | |
|---|---|---|
| 7,015,315 B1 | 3/2006 | Cook et al. |
| 7,101,993 B1 | 9/2006 | Cook et al. |
| 7,214,695 B2 | 5/2007 | Kelly et al. |
| 7,214,696 B2 | 5/2007 | Kelly et al. |
| 7,560,488 B2 | 7/2009 | Kelly et al. |
| 8,058,069 B2 | 11/2011 | Yaworski et al. |
| 8,101,743 B2 | 1/2012 | Brown-Driver et al. |
| 8,158,601 B2 | 4/2012 | Chen et al. |
| 8,168,663 B2 | 5/2012 | Kelly et al. |
| 8,168,775 B2 | 5/2012 | Sah et al. |
| 8,334,373 B2 | 12/2012 | Vornlocher et al. |
| 8,362,231 B2 | 1/2013 | Tuschl et al. |
| 8,372,968 B2 | 2/2013 | Tuschl et al. |
| 8,492,359 B2 | 7/2013 | Yaworski et al. |
| 8,552,171 B2 | 10/2013 | Tuschl et al. |
| 8,642,076 B2 | 2/2014 | Manoharan et al. |
| 8,653,119 B2 | 2/2014 | Kelly et al. |
| 8,697,860 B1 | 4/2014 | Monia et al. |
| 8,741,866 B2 | 6/2014 | Sah et al. |
| 8,778,902 B2 | 7/2014 | Tuschl et al. |
| 8,802,644 B2 | 8/2014 | Chen et al. |
| 8,822,668 B2 | 9/2014 | Yaworski et al. |
| 8,895,718 B2 | 11/2014 | Tuschl et al. |
| 8,895,721 B2 | 11/2014 | Tuschl et al. |
| 9,061,044 B2 | 6/2015 | Freier |
| 9,193,753 B2 | 11/2015 | Tuschl et al. |
| 9,234,196 B2 | 1/2016 | Sah et al. |
| 9,249,112 B2 | 2/2016 | Labaudiniere et al. |
| 9,364,435 B2 | 6/2016 | Yaworski et al. |
| 9,399,774 B2 | 7/2016 | Monia et al. |
| 9,567,582 B2 | 2/2017 | Tuschl et al. |
| 9,770,441 B1 | 9/2017 | Girard et al. |
| 9,943,538 B1 | 4/2018 | Crooke |

(Continued)

FOREIGN PATENT DOCUMENTS

| | | |
|---|---|---|
| WO | 2016033326 | 3/2016 |
| WO | 2018112320 | 6/2018 |
| WO | 2019060442 | 3/2019 |

OTHER PUBLICATIONS

Cruz, Marcia W., et al., "A Review of Tafamidis for the Treament of Transthyretin-Related Amyloidosis", Neurol Ther, 2015, pp. 61-79, vol. 4.

Adamski-Werner, Sara L., et al., "Diflunisal Analogues Stabilize the Native State of Transthyretin. Potent Inhibition of Amyloidogenesis", Journal of Medicinal Chemistry, 2004, pp. 355-374, vol. 47.

Alexander, Kevin M., et al., "Novel pharmacotherapies for cardiac amyloidosis", Pharmacology and Therapeutics, Jun. 22, 2017, pp. 129-138, vol. 180.

Anonymous, "History of Changes for Study: NCT03759379 Study Record Versions Version A B Submitted Date Changes History of Changes for Study: NCT03759379 HELIOS-A: A Study of Vutrisiran (ALN-TTRSC02) in Patients with Hereditary Transthyretin Amyloidosis (hATTR Amylo Study NCT03759379", Clincial trials.gov, https://clinicaltrials.gov/ct2/history/NCT03759379?V_4=View#StudyPageTop, pp. 1-4.

(Continued)

*Primary Examiner* — Raymond J Henley, III
(74) *Attorney, Agent, or Firm* — John A. Wichtowski (57) ABSTRACT

The present invention relates to pharmaceutical compositions and methods of treatment comprising administering to a patient in need thereof a combination of a benzoxazole derivative transthyretin stabilizer or a pharmaceutically acceptable salt or prodrug thereof and an additional therapeutic agent for the treatment of transthyretin amyloidosis. Particularly, the present invention relates to pharmaceutical compositions and methods of treatment comprising administering to a patient in need thereof 2-(3,5-dichlorophenyl)-1,3-benzoxazole-6-carboxylic acid or a pharmaceutically acceptable salt or prodrug thereof and one or more additional therapeutic agent for the treatment of transthyretin amyloidosis.

5 Claims, 2 Drawing Sheets

(56) References Cited

U.S. PATENT DOCUMENTS 9,943,539 B1  4/2018  Crooke

OTHER PUBLICATIONS

Benson, Merrill D., et al., "Inotersen Treatment for Patiens with Hereditary Transthyretin Amyloidosis", The New England Journal of Medicine, Jul. 5, 2018, pp. 22-31, 379(1).

Castano, Adam, et al., "Natural history and therapy of TTR-cardiac amyloidosis: emerging disease-modifying therapies from organ transplantation to stabilizer and silencer drugs", Heart Failure Review, Kluwer Academic Publishers, Nov. 19, 2014, pp. 163-178, 20(2).

Coelho, Teresa, et al., "Mechanism of Action and Clinical Application of Tafamidis in Hereditary Transthyretin Amyloidosis", Neurol Ther., 2016, pp. 1-25, vol. 5.

Fritschka, Max, et al., "Unusal case of ATTR amyloidosis with cardiac manifestation and situs inversus totalis", Clincial Research in Cardiology, Berlin Heidelberg, Jan. 23, 2017, pp. 311-316, 106(4).

Gillmore, Julian D., et al., "A Phase 2 Multi-Center, Open-Label Trial to Evaluate the Safety, Pharmacokinetics, Pharmacodynamics and Exploratory Clinical Activity of Revusiran (ALN-TTRsc), and RNAi Therapeutic for the Treatment of Patients with Transthyretin Cardiac Amyloidosis", https://www.alnylam.com/web/assets/Revusiran-ACC-15Mar2015.pdf XP055679555, Mar. 15, 2015, 14 pages.

Gonalves, et al., "Glial cells in familial amyloidotic poyneuropathy", Acta Neuropathologica Communications, 2014, pp. 1-25, vol. 2.

Green, Nora S., et al., "Synthesis and Characterization of Potent Bivalent Amyloidosis Inhibitors That Bind Prior to Transthyretin Tetramerization", Journal American Chemical Society, 2003, pp. 13404-13414, vol. 125.

Hawkins, Philip N., et al., "Evolving landscape in the management of transthyretin amyloidosis", Annals of Medicine, Nov. 17, 2015, pp. 625-638, 47(8).

International Written Opinion and Search Report mailed on Jul. 6, 2020 for Application No. PCT/IB2019/060899, filed on Dec. 17, 2019, 26 pages.

Maurer, Mathew S., et al., "Tafamidis in Transthyretin Amyloid Cardiomyopathy Effects on Transthyretin Stablizatoin and Clinical Outcomes", Circulation Heart Failure, 2015, pp. 519-526, 8(3).

Oza, Vibha B., et al., "Synthesis, Structure, and Acitvity of Disclofenac Analogues as Transthyretin Amyloid Fibril Formation Inhibitors", Journal of Medicinal Chemistry, 2002, pp. 321-332, 45(2).

Petrassi, H. Michael, et al., "Structure-Based Design of N-Phenyl Phenoxazine Transthyretin Amyloid Fibril Inhibitors", Journal American Chemical Society, 2000, pp. 2178-2192, vol. 122.

Razavi, Hossein, et al., "Benzoxazoles as Transthyretin Amyloid Fibril Inhibitors: Synthesis, Evaluation, and Medchanism of Action", Angew. Chem, 2003, pp. 2864-2867, vol. 105.

Richards, Duncan B., et al.,"Repeat doses of anitbody to serum amyloid p. Component clear amyloid deposits in patients with systemic amyloidosis", Science Translational Medicine Report, Jan. 3, 2018, pp. 1-8, 10(422).

Saelices, Lorena, et al., "Uncovering the Mechanism of Aggregation of Human Transthyretin", Journal of Biological Chemistry, 2015, pp. 28932-28943, 290(48).

Verona, Gulielmo, et al., "Inhibition of the mechano-enzymatic amyloidogenssis of transthyretin: role of ligand affinty, binding cooperativity and occupancy of the inner channel", Nature—Scientific Reports, 2017—pp. 1-7, 7(182).

Onpattro—Annex—I thru IV—Summary of Product Characteristics, 34 pages.

Teqsedi—Annex—I thru IV—Summary of Product Characteristics, 39 pages.

FIG. 1

Black = 2-(2,6-dichlorophenyl)benzo[d]oxazole-6-carboxylic acid
Gray = 2-(3,5-dichlorophenyl)benzo[d]oxazole-5-carboxylic acid
White = 3-(5-(2-fluorophenyl)-1,2,4-oxadiazol-3-yl)benzoic acid

FIG. 2

Black = 2-(2,6-dichlorophenyl)benzo[d]oxazole-6-carboxylic acid
Gray = 2-(3,5-dichlorophenyl)benzo[d]oxazole-5-carboxylic acid
White = 3-(5-(2-fluorophenyl)-1,2,4-oxadiazol-3-yl)benzoic acid

PHARMACEUTICAL COMPOSITIONS AND METHODS COMPRISING A COMBINATION OF A BENZOXAZOLE TRANSTHYRETIN STABILIZER AND AN ADDITIONAL THERAPEUTIC AGENT

This application is a national stage application under 35 U.S.C. 371 of PCT//IB2019/060899, filed on Dec. 17, 2019, which claims the benefit of U.S. Provisional Patent Application No. 62/782,403, filed on Dec. 20, 2018, the disclosures of which are hereby incorporated by reference in their entirety.

FIELD OF THE INVENTION

The present invention relates to pharmaceutical compositions and methods of treatment comprising administering to a patient in need thereof a combination of a benzoxazole derivative transthyretin stabilizer or a pharmaceutically acceptable salt or prodrug thereof and one or more additional therapeutic agent. Particularly, the present invention relates to pharmaceutical compositions and methods of treatment comprising administering to a patient in need thereof 2-(3,5-dichlorophenyl)-1,3-benzoxazole-6-carboxylic acid or a pharmaceutically acceptable salt or prodrug thereof and one or more additional therapeutic agent. The compositions and methods of the invention are useful in stabilizing transthyretin, inhibiting transthyretin misfolding, proteolysis, and treating amyloid diseases associated thereto.

BACKGROUND OF THE INVENTION

Transthyretin (TTR) is a 55 kDa homotetrameric protein present in serum and cerebral spinal fluid and which functions as a transporter of L-thyroxine (T4) and holo-retinol binding protein (RBP). TTR has been found to be an amyloidogenic protein that, under certain conditions, can be transformed into fibrils and other aggregates which can lead to disease pathology such as polyneuropathy or cardiomyopathy in humans.

U.S. Pat. Nos. 7,214,695; 7,214,696; 7,560,488; 8,168,683; and 8,653,119 each of which is incorporated herein by reference, discloses benzoxazole derivatives which act as transthyretin stabilizers and are of the formula or a pharmaceutically acceptable salt thereof; wherein Ar is 3,5-difluorophenyl, 2,6-difluorophenyl, 3,5-dichlorophenyl, 2,6-dichlorophenyl, 2-(trifluoromethyl)phenyl or 3-(trifluoromethyl)phenyl. Particularly, 2-(3,5-dichlorophenyl)-1,3-benzoxazole-6-carboxylic acid (tafamidis) of the formula is disclosed therein. Tafamidis is an orally active transthyretin stabilizer that inhibits tetramer dissociation and proteolysis that has been approved in certain jurisdictions for the treatment of transthyretin polyneuropathy (TTR-PN) and is currently in development for the treatment of transthyretin cardiomyopathy (TTR-CM). U.S. Pat. No. 9,249,112, also incorporated herein by reference, discloses polymorphic forms of the meglumine salt of 2-(3,5-dichlorophenyl)-1,3-benzoxazole-6-carboxylic acid (tafamidis meglumine). U.S. Pat. No. 9,770,441 discloses polymorphic forms of the free acid of 2-(3,5-dichlorophenyl)-1,3-benzoxazole-6-carboxylic acid (tafamidis), and is also incorporated by reference herein.

SUMMARY OF THE INVENTION

The present invention provides pharmaceutical compositions and methods comprising the compound 2-(3,5-dichlorophenyl)-1,3-benzoxazole-6-carboxylic acid or a pharmaceutically acceptable salt or prodrug thereof, and one or more additional therapeutic agent. Particular embodiments of this invention are pharmaceutical compositions and methods comprising 2-(3,5-dichlorophenyl)-1,3-benzoxazole-6-carboxylic acid or a pharmaceutically acceptable salt or prodrug thereof, and one or more additional therapeutic agents selected from the group consisting of agents that lower plasma levels of TTR such as an antisense therapy, TTR gene editing therapy, transcriptional modulators, translational modulators, TTR protein degraders and antibodies that bind and reduce TTR levels; amyloid reduction therapies such as anti-amyloid antibodies (either TTR selective or general), stimulators of amyloid clearance, fibril disruptors and therapies that inhibit amyloid nucleation; other TTR stabilizers; and TTR modulators such as therapeutics which inhibit TTR cleavage. Particularly, the present invention provides pharmaceutical compositions and methods comprising tafamidis or tafamidis meglumine salt with one or more additional therapeutic agents. More particularly, the present invention provides pharmaceutical compositions and methods comprising a polymorphic form of tafamidis free acid or a polymorphic form of tafamidis meglumine salt with one or more additional therapeutic agents.

The present invention also provides a method of treating or preventing transthyretin amyloidosis in a patient, the method comprising administering to a patient in need thereof a therapeutically or prophylactically effective amount of 2-(3,5-dichlorophenyl)-1,3-benzoxazole-6-carboxylic acid or a pharmaceutically acceptable salt or prodrug thereof, and one or more additional therapeutic agents.

A particular embodiment of the present method of treatment is the method wherein a pharmaceutical composition comprising 2-(3,5-dichlorophenyl)-1,3-benzoxazole-6-carboxylic acid or a pharmaceutically acceptable salt or prodrug thereof, and one or more additional therapeutic agent are administered orally. Additional embodiments of this invention are methods of treatment as described above wherein the 2-(3,5-dichlorophenyl)-1,3-benzoxazole-6-carboxylic acid or a pharmaceutically acceptable salt or prodrug thereof, and one or more additional therapeutic agent are administered parenterally (intravenously or subcutaneously). Further embodiments of this invention are methods of treatment wherein the 2-(3,5-dichlorophenyl)-1,3-benzoxazole-6-carboxylic acid or a pharmaceutically acceptable salt or prodrug thereof is administered orally and the one or more additional therapeutic agent is administered either orally or parenterally. Another embodiment of the present invention is wherein a pharmaceutical composition comprising 2-(3,5-dichlorophenyl)-1,3-benzoxazole-6-carboxylic acid or a pharmaceutically acceptable salt or prodrug thereof in combination with one or more additional therapeutic agent is administered parenterally and then 2-(3,5-dichlorophenyl)-1,3-benzoxazole-6-carboxylic acid or a pharmaceutically acceptable salt or prodrug thereof is administered orally. A particular method of treatment is a method of treating TTR amyloidosis such as TTR polyneuropathy or TTR cardiomyopathy, the method comprising administering to a patient in need thereof a therapeutically effective amount of 2-(3,5-dichlorophenyl)-1,3-benzoxazole-6-carboxylic acid or a pharmaceutically acceptable salt or prodrug thereof in combination with one or more additional therapeutic agents.

DETAILED DESCRIPTION OF THE INVENTION

The present invention provides methods for treating a TTR-associated disease in a human subject, such as a transthyretin-mediated amyloidosis (ATTR amyloidosis), e.g., hereditary ATTR (h-ATTR) or non-hereditary ATTR (wt-ATTR). The methods include administering to the subject a therapeutically effective amount of tafamidis or a pharmaceutically acceptable salt thereof in combination with a therapeutically effective amount or prophylactically effective amount of another therapeutic agent.

In one aspect, the present invention provides methods of treating a human subject suffering from a TTR-associated disease or at risk for developing a TTR-associated disease. The methods include administering to the human subject a 10 mg to about 100 mg (e.g., about 10, 20, 30, 35, 40, 50, 60, 70, 80, 90 or about 100 mg) of tafamidis or a pharmaceutically acceptable salt thereof in combination with a therapeutically effective amount of one or more additional therapeutic agents.

Another aspect of the present invention provides methods of improving at least one indicia of cardiac impairment or quality of life in a human subject suffering from a TTR-associated disease or at risk for developing a TTR-associated disease.

In another aspect, the present invention provides methods of improving at least one indicia of neurological impairment or quality of life in a human subject suffering from a TTR-associated disease or at risk for developing a TTR-associated disease.

In another aspect, the present invention provides methods of reducing, slowing, or arresting a Neuropathy Impairment Score (NIS) or a modified NIS (mNIS+7) in a human subject suffering from a TTR-associated disease or at risk for developing a TTR-associated disease. The methods include administering to the human subject a fixed dose of about 10 mg to about 100 mg (e.g., about 10, 20, 30, 35, 40, 50, 60, 70, 80, 90 or about 100 mg) of tafamidis or a pharmaceutically acceptable salt thereof in combination with a therapeutically effective amount of one or more additional therapeutic agent.

In another aspect, the present invention provides methods of increasing a 6-minute walk test (6MWT) in a human subject suffering from a TTR-associated disease or at risk for developing a TTR-associated disease. The methods include administering to the human subject a fixed dose of about 10 mg to about 100 mg (e.g., about 10, 20, 30, 35, 40, 50, 60, 70, 80, 90 or about 100 mg) of tafamidis or a pharmaceutically acceptable salt thereof in combination with a therapeutically effective amount of one or more additional therapeutic agent.

In an embodiment, the subject is a human being treated or assessed for a disease, disorder or condition that would benefit from reduction in TTR dissociation and/or proteolysis; a human at risk for a disease, disorder or condition that would benefit from reduction in TTR dissociation; a human having a disease, disorder or condition that would benefit from reduction in TTR dissociation; and/or human being treated for a disease, disorder or condition that would benefit from reduction in TTR dissociation.

In some embodiments, the human subject is suffering from a TTR-associated disease. In other embodiments, the subject is a subject at risk for developing a TTR-associated disease, e.g., a subject with a TTR gene mutation that is associated with the development of a TTR-associated disease (e.g., before the onset of signs or symptoms suggesting the development of TTR amyloidosis such as TTR-cardiomyopathy or TTR-polyneuropathy), a subject with a family history of TTR-associated disease (e.g., before the onset of signs or symptoms suggesting the development of TTR amyloidosis), or a subject who has signs or symptoms suggesting the development of TTR amyloidosis.

A "TTR-associated disease," as used herein, includes any disease caused by or associated with the formation of non-tetrameric species including but not limited to monomers, dimers, aggregates and amyloid deposits in which these species consist of variant or wild-type TTR protein. Mutant and wild-type TTR give rise to various forms of amyloid deposition (amyloidosis). Amyloidosis involves the formation and aggregation of misfolded proteins, resulting in extracellular deposits that impair organ function. Clinical syndromes associated with TTR aggregation include, for example, senile systemic amyloidosis (SSA); systemic familial amyloidosis; familial amyloidotic polyneuropathy (FAP); familial amyloidotic cardiomyopathy (FAC); and leptomeningeal amyloidosis, also known as leptomeningeal or meningocerebrovascular amyloidosis, central nervous system (CNS) amyloidosis, or amyloidosis VII form. TTR amyloidosis can impact various organs and systems and manifest in the cardiac system as heart failure or arrhythmia, in the gastrointestinal system as diarrhea, nausea or vomiting; in the genitourinary system as proteinuria, kidney impairment or kidney failure, urinary tract infections, incontinence or impotence; in the autonomic system as falls, lightheadedness or weight loss; and in the peripheral nervous system as numbness/tingling, pain, weakness or impaired mobility. Transthyretin derived amyloidosis has also been implicated as a probable cause of lumbar spinal stenosis (see Westermark, P. et. al. Ups J Med Sci 2014 August, 119(3), 223-228) and as a cause of knee joint osteoarthritis (see Takanashi, T. et. al. Amyloid 2013 September, 20(3) 151-155).

In one embodiment, tafamidis or a pharmaceutically acceptable salt thereof in combination with a therapeutically effective amount of one or more additional therapeutic agents are administered to subjects suffering from familial amyloidotic cardiomyopathy (FAC). In another embodiment, tafamidis or a pharmaceutically acceptable salt thereof in combination with a therapeutically effective amount of one or more additional therapeutic agents are administered to subjects suffering from FAC with a mixed phenotype, i.e., a subject having both cardiac and neurological impairments. In yet another embodiment, tafamidis or a pharmaceutically acceptable salt thereof in combination with a therapeutically effective amount of one or more additional therapeutic agents are administered to subjects suffering from FAP with a mixed phenotype, i.e., a subject having both neurological and cardiac impairments. In another embodiment, tafamidis or a pharmaceutically acceptable salt thereof in combination with a therapeutically effective amount of one or more additional therapeutic agents are administered to subjects suffering from FAP that has been treated with an orthotopic liver transplantation (OLT). In another embodiment, tafamidis or a pharmaceutically acceptable salt thereof in combination with a therapeutically effective amount of one or more additional therapeutic agents are administered to subjects suffering from senile systemic amyloidosis (SSA). In other embodiment of the methods of the invention, tafamidis or a pharmaceutically acceptable salt thereof in combination with a therapeutically effective amount of one or more additional therapeutic agents are administered to subjects suffering from familial amyloidotic cardiomyopathy (FAC) and senile systemic amyloidosis (SSA). Normal-sequence TTR causes cardiac amyloidosis in people who are elderly and is termed senile systemic amyloidosis (SSA) (also called senile cardiac amyloidosis (SCA) or cardiac amyloidosis). SSA often is accompanied by microscopic extracellular deposits in many other organs.

TTR mutations can accelerate the process of TTR amyloid formation and are the most important risk factor for the development of clinically significant TTR amyloidosis (also called ATTR (amyloidosis-transthyretin type)). Numerous amyloidogenic TTR variants are known to cause systemic familial amyloidosis.

In some embodiments of the methods of the invention, tafamidis or a pharmaceutically acceptable salt thereof in combination with a therapeutically effective amount of one or more additional therapeutic agents are administered to subjects suffering from transthyretin (TTR)-related familial amyloidotic polyneuropathy (FAP). Such subjects may suffer from ocular manifestations, such as vitreous opacity and glaucoma. It is known to one of skill in the art that amyloidogenic transthyretin (ATTR) synthesized by retinal pigment epithelium (RPE) plays important roles in the progression of ocular amyloidosis. Previous studies have shown that pan-retinal laser photocoagulation, which reduced the RPE cells, prevented the progression of amyloid deposition in the vitreous, indicating that the effective suppression of ATTR expression in RPE may become a novel therapy for ocular amyloidosis (see, e.g., Kawaji, T., et al., Ophthalmology. (2010) 117: S52-S55).

The methods of the invention are useful for treatment of ocular manifestations of TTR related FAP, e.g., ocular amyloidosis. The tafamidis or a pharmaceutically acceptable salt thereof in combination with a therapeutically effective amount of one or more additional therapeutic agents can be delivered in a manner suitable for targeting a particular tissue, such as the eye. Modes of ocular delivery include retrobulbar, subcutaneous eyelid, subconjunctival, subtenon or anterior chamber injection or can be formulated into an appropriate solution or suspension for use as eye drops or can be formulated as an ocular ointment.

The pharmaceutical combinations and methods of the present invention comprise tafamidis or a pharmaceutically acceptable salt thereof and therapeutic agents that lower plasma levels of TTR. When an additional therapeutic agent that lowers plasma TTR levels is employed any residual TTR in the plasma can be stabilized by tafamidis or a pharmaceutically acceptable salt thereof and thereby confer a beneficial effect to the patient. Additional therapeutic agents that can be employed in the pharmaceutical combinations and methods of the present invention include, but are not limited to, agents which lower TTR levels in a patient such as antisense therapies, gene editing therapies (e.g. CRISPR), transcriptional modulators (e.g. BET inhibitors), translational modulators (e.g. translational stalling), protein degraders (e.g. ER modulators, MODA) and antibodies that bind and reduce TTR levels.

The pharmaceutical combinations and methods of the present invention comprise tafamidis or a pharmaceutically acceptable salt thereof and additional therapeutic agents that stabilize transthyretin or are amyloid reduction therapies. The existing amyloid can be reduced and/or cleared by the amyloid reducing therapeutic agent, while tafamidis or a pharmaceutically acceptable salt thereof can stabilize TTR, resulting in decreased generation of additional amyloid. Additional therapeutic agents that reduce amyloid include, but are not limited to, anti-amyloid antibodies (TTR selective antibodies or general anti-amyloid antibodies e.g. Prothena PRX-004), stimulators of amyloid clearance, therapeutic agents which cap and inhibit growth of amyloid fibers and therapeutic agents that inhibit amyloid nucleation.

The pharmaceutical combinations and methods of the present invention also comprise tafamidis or a pharmaceutically acceptable salt thereof and additional therapeutic agents that are TTR stabilizers. In certain embodiments the TTR stabilizers are whose binding is not mutually exclusive with tafamidis and which can increase overall tetramer stabilization effect. Small molecule compounds which act as TTR stabilizers and can be used as additional therapeutic agents in the pharmaceutical compositions and methods of the present invention include, but are not limited to, diflunisal, tolcapone, genistein, curcumin, PTI-110, and AG10 and analogues thereof.

diflunisal

Eidos Therapeutics' AG10 and analogues thereof can be prepared as described in WO 2014100227, U.S. Pat. Nos. 9,169,214, 9,642,838, 9,913,826 and Miller, M. et al. J. Med. Chem. available August 2018 at DOI:10.1021/acs.jmedchem.8b00817 each of which is incorporated herein by reference in its entirety. AG10 and salts thereof and polymorphic forms of those salts as well as processes for their preparation have also been disclosed in US 20180237396 and WO 18151815 each of which are incorporated herein by reference in its entirety.

AG10 and Analogues

Additional compounds that can be used in combination with tafamidis or a pharmaceutically acceptable salt thereof in the pharmaceutical compositions and methods of this invention include the following compounds and their pharmaceutically acceptable salts:

The pharmaceutical combinations and methods of the present invention also comprise tafamidis or a pharmaceutically acceptable salt thereof and additional therapeutic agents which act as TTR modulators that can block the ability of TTR to incorporate into fibrils. Stabilization of TTR with tafamidis and inhibition of TTR incorporation into fibrils with additional therapeutic agent(s) can have combinatorial benefit.

Representative examples of additional therapeutic agents that can act as TTR fibril disruptors in the compositions and methods of the present invention include doxycycline optionally in combination with tauroursodeoxycholic acid. Doxycycline has been found to have amyloid fibril disrupting activity in a murine in vitro model (Cardoso, I. et. al; The FASEB Journal 2003, 17, 803-809 and Cardoso, I. et. al. The FASEB Journal 2006, 20, 234-239) and the combination of doxycycline and tauroursodeoxycholic acid was shown to have beneficial effect in a Val30Met transgenic mouse model. Another additional therapeutic agent that can be employed as a TTR fibril disruptor in combination with tafamidis in the compositions and methods of the present invention is epigallocathechin (EGCG), the active ingredient in green tea extract, which has been shown to bind to amyloidogenic light chains and prevent fibril formation (Hora, M. et. al. Scientific Reports 2017, 7, 41515.

Ataluren (formerly known as PTC124), which is chemically named as 3-[5-(2-fluorophenyl)-1,2,4-oxadiazol-3-yl] benzoic acid, is an orally administered small-molecule compound for the treatment of patients with genetic disorders (e.g., Duchenne muscular dystrophy (DMD) and cystic fibrosis) caused due to a nonsense mutation. Ataluren which was discovered and designed by PTC Therapeutics, Inc. and is sold under the trade name Translarna in the European Union. Translarna is the first treatment approved for the underlying cause of DMD and the European Medicines Agency (EMA) has designated ataluren as an orphan medicinal product. Ataluren, or a pharmaceutically acceptable salt thereof has been found to inhibit TTR fibril formation and can be used in combination with tafamidis or a pharmaceutically acceptable salt thereof in the compositions and methods of the present invention. Ataluren can be prepared as described in WO 2006/110483, U.S. Pat. Nos. 7,678,922 and 8,367,841, WO 2017222474 and US 20170362192; each of which is incorporated herein by reference in its entirety.

Ataluren can be administered orally, in certain instances every day in 3 doses. For example, the first dose can be taken in the morning, the second at midday, and the third in the evening. Recommended dosing intervals are 6 hours between morning and midday doses, 6 hours between midday and evening doses, and 12 hours between the evening dose and the first dose on the next day. The recommended dose of ataluren is 10 mg/kg body weight in the morning, 10 mg/kg body weight at midday, and 20 mg/kg body weight in the evening (for a total daily dose of ataluren of 40 mg/kg body weight).

A representative dosage form for ataluren is sachets of 125 mg, 250 mg or 1000 mg. For administration of tafamidis or a pharmaceutically acceptable salt thereof together with ataluren in a single dosage form each sachet can also contain 1 mg to 50 mg of tafamidis or a pharmaceutically acceptable salt thereof. For example, each sachet can contain 20 mg of tafamidis meglumine or 15.25 mg tafamidis free acid together with 125 mg, 250 mg or 1000 mg of ataluren. The contents of each sachet can be dissolved or suspended in liquid or mixed with food and taken orally. Alternatively, the tafamidis or a pharmaceutically acceptable salt thereof can be taken in a separate dosage form, such as an oral gel cap, and the ataluren can be taken orally as a solution or suspension or mixed with food. A representative method is to administer tafamidis or a pharmaceutically acceptable salt thereof once a day, for example as an oral gel cap, and to administer the ataluren three times a day as described above.

Another embodiment of the present invention are compositions and methods for treating transthyretin amyloidosis comprising tafamidis in combination with additional therapeutic agent(s) that deplete circulating levels of serum amyloid P component (SAP) an/or an anti-SAP antibody or an antigen binding fragment of an anti-SAP antibody. Representative therapeutic agents that reduce circulating levels of serum amyloid P component include D-Proline derivatives such as those disclosed in U.S. Pat. Nos. 7,045,499; 7,691,687 and 9,192,668, each of which are incorporated herein by reference in its entirety. A particular additional therapeutic agent useful in the compositions and methods of the present invention is the compound (2R)-1-[6-[(2R)-2-carboxypyrrolidin-1-yl]-6-oxohexanoyl]pyrrolidine-2-carboxylic acid, also known as CPHCP and miridesap, which is disclosed in U.S. Pat. No. 7,045,499. A particular anti-SAP antibody which can be used in the compositions and methods of the present invention is dezamizumab which is disclosed in U.S. Pat. No. 9,192,668. The pharmaceutical combinations and methods of the present invention also comprise tafamidis or a pharmaceutically acceptable salt thereof and additional therapeutic agents which act as inhibitors of TTR cleavage.

Therapeutic agents that reduce the level of TTR in a patient include transthyretin silencers such as small-interfering RNAs and anti-sense oligonucleotides. Transthyretin silencers (TTR silencers) are a class of drug which can be used as an additional therapeutic agent in the compositions and methods of the present invention. TTR silencers include both small-interfering RNAs (siRNAs) and antisense oligonucleotides. The TTR silencers can localize to the liver and suppress the production of transthyretin, thereby lessening the amount of transthyretin that is available to dissociate, misfold and form amyloid. Tafamidis or a pharmaceutically acceptable salt thereof can be combined with a TTR silencer to provide the pharmaceutical compositions of the present invention. Tafamidis or a pharmaceutically acceptable salt thereof can be used together with a TTR silencer in the methods of the present invention.

One class of TTR silencer useful in the compositions and methods of the present invention is small-interfering RNAs, such as patisiran. Patisiran is a double-stranded small-interfering ribonucleic acid (siRNA), marketed by Alnylam as ONPATTRO® and formulated as a lipid complex for delivery to hepatocytes. Patisiran is disclosed in U.S. Pat. Nos. 8,168,775; 8,741,866 and 9,234,196 as well as corresponding WO 2010048228; each of which is incorporated herein by reference in its entirety. The molecular formula of patisiran sodium is $C_{412} H_{480} N_{148} Na_{40} O_{290} P_{40}$ and the molecular weight is 14304 Da. Patisiran specifically binds to a genetically conserved sequence in the 3' untranslated region (3'UTR) of mutant and wild-type transthyretin (TTR) messenger RNA (mRNA) thereby degrading the TTR mRNA which results in a reduction of serum TTR. A representative pharmaceutical composition of the present invention is a homogeneous solution for intravenous infusion wherein the solution comprises tafamidis or a pharmaceutically acceptable salt thereof and patisiran. For example, each 1 mL of solution contains 2 mg of patisiran (equivalent 2.1 mg of patisiran sodium). Each 1 mL also contains 6.2 mg cholesterol USP, 13.0 mg (6Z,9Z,28Z,31Z)-heptatriaconta-6,9,28,31tetraen-19-yl-4-(dimethylamino) butanoate (DLin-MC3-DMA), 3.3 mg 1,2-distearoyl-sn-glycero-3-phosphocholine (DSPC), 1.6 mg α-(3'-{[1,2-di(myristyloxy) propanoxy]carbonylamino}propyl)-w-methoxy, polyoxyethylene (PEG2000C-DMG), 0.2 mg potassium phosphate monobasic anhydrous NF, 8.8 mg sodium chloride USP, 2.3 mg sodium phosphate dibasic heptahydrate USP, and Water for Injection USP and the total solution pH is ~7.0 and contains 10 mg to 200 mg of tafamidis or a pharmaceutically acceptable salt thereof. The recommended dosage for patisiran is 0.3 mg/kg once every three weeks for patients weighing less than 100 kg and 30 mg once every three weeks for patients weighing 100 kg or more.

Other siRNAs, such as the GalNAc-siRNA conjugates designated as ALN-TTRsc, also known as revusiran, and ALN-TTRsc02 can be used in the pharmaceutical compositions and methods of the present invention. ALN-TTRsc and ALN-TTRsc-02 can be administered subcutaneously. WO 2018112320, incorporated by reference herein, describes various GalNAc-siRNA conjugates that can be used in the pharmaceutical compositions and methods of the present invention. In the combinations and methods of the present invention ALN-TTRsc02 can be administered together with tafamidis or a pharmaceutically acceptable salt thereof in a single dosage form such as a subcutaneous formulation. Alternatively, ALN-TTRsc02 and tafamidis or a pharmaceutically acceptable salt thereof can be administered separately, such as administering a subcutaneous formulation of ALN-TTRsc02 and an oral administration of tafamidis or a pharmaceutically acceptable salt thereof. An embodiment of the present invention is to administer ALN-TTRsc02 subcutaneously once every three months and to administer tafamidis or a pharmaceutically acceptable salt thereof daily. The dosage of ALN-TTRsc02 to be administered can vary from 5 mg to 300 mg, with a particular dosage being 25 mg administered once every 3 months. Particular dosages of tafamidis meglumine and tafamidis free acid are 80 mg and 61 mg, respectively, administered once daily.

Another class of TTR silencers useful in the compositions and methods of the present invention are antisense oligonucleotides, such as inotersen. Inotersen which is marketed as Tegsedi® by Ionis Pharmaceuticals Inc is an 'antisense oligonucleotide', a very short piece of synthetic DNA designed to attach to the genetic material of the cells responsible for producing the transthyretin protein. Inotersen decreases transthyretin production, thereby reducing the formation of amyloids and relieving the symptoms of hATTR. Inotersen has a molecular weight of 7183 g/mol and formula $C_{230}H_{318}N_{69}O_{121}P_{19}S_{19}$. Inotersen is described in U.S. Pat. Nos. 8,697,860; 9,061,044; 9,399,774 and 9,816,092 and in WO 2011139917, each of which is incorporated by reference herein. A pharmaceutical composition of the present invention comprising tafamidis or a pharmaceutically acceptable salt thereof and inotersen can be administered as an aqueous solution. A method of the present invention is administration of a pharmaceutical composition comprising tafamidis or a pharmaceutically acceptable salt thereof and inotersen as an aqueous solution to a patient in need thereof. Alternatively, tafamidis or a pharmaceutically acceptable salt thereof can be administered orally and inotersen can be administered subcutaneously. For example, tafamidis meglumine or tafamidis free acid can be administered orally once a day and inotersen can be administered subcutaneously once a week. The tafamidis meglumine or tafamidis free acid, at 80 mg and 61 mg dosages, respectively, can be administered once every day or alternatively once a day on the days in between when inotersen is administered subcutaneously. Inotersen can be administered subcutaneously as an aqueous solution of its sodium salt at a dosage of 300 mg inotersen sodium which is equivalent to 284 mg of inotersen.

Another embodiment of the present invention is the use of tafamidis or a pharmaceutically acceptable salt thereof in combination with a gene editing therapy to treat TTR amyloidoses. A representative gene editing therapy that can be used in combination with tafamidis is Regeneron/Intellia's NTLA-1001 modular lipid nanoparticle CRISPR/Cas9 comprised of a single guide RNA, mRNA encoding S.py Cas9 and an encapsulating lipid formulation. U.S. Pat. No. 10,000,722, incorporated herein by reference, describes CRISPR/Cas9 gene editing technology used in conjunction with lipid nanoparticle encapsulation delivery technology to provide NTLA-1001.

In a preferred embodiment, the methods of treatment using the combination of tafamidis or a pharmaceutically acceptable salt thereof and an additional therapeutic agent are for the treatment of TTR cardiomyopathy or TTR polyneuropathy.

In the treatment of TTR amyloidosis with combination therapy with 2-(3,5-dichlorophenyl)-1,3-benzoxazole-6-carboxylic acid or a pharmaceutically acceptable salt or prodrug thereof, and an additional therapeutic agent is particularly advantageous and produces a synergistic effect in treating the TTR amyloidosis when compared to the administration of either agent alone.

It is noted that when compounds are discussed herein, it is contemplated that the compounds may be administered to a patient as a pharmaceutically acceptable salt, prodrug, or a salt of a prodrug. All such variations are intended to be included in the invention.

The term "patient in need thereof" means humans and other animals who have or are at risk of having a TTR amyloidosis such as senile systemic amyloidosis (SSA); systemic familial amyloidosis; familial amyloidotic polyneuropathy (FAP); familial amyloidotic cardiomyopathy (FAC); and leptomeningeal amyloidosis, also known as leptomeningeal or meningocerebrovascular amyloidosis, central nervous system (CNS) amyloidosis, or amyloidosis VII form.

The term "treating", "treat" or "treatment" as used herein includes preventative (e.g., prophylactic), palliative, adjuvant and curative treatment. For example, the treatment of familial amyloidotic polyneuropathy (FAP) or familial amyloidotic cardiomyopathy (FAC), as used herein means that a patient having familial amyloidotic polyneuropathy (FAP) or familial amyloidotic cardiomyopathy (FAC) or at risk of having familial amyloidotic polyneuropathy (FAP) or familial amyloidotic cardiomyopathy (FAC) can be treated according to the methods described herein. For patients undergoing preventative treatment, a resulting reduction in the incidence of the disease state being preventively treated is the measurable outcome of the preventative treatment.

By "pharmaceutically acceptable" it is meant the carrier, diluent, excipients, and/or salts or prodrugs must be compatible with the other ingredients of the formulation, and not deleterious to the patient.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, when a compound used in the compositions and methods of the present invention contains a carboxylic acid functional group (such as tafamidis), a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-

C₃)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, when a compound used in the compositions and methods of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1-(($C_1$-$C_6$)alkanoyloxy) ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

When a compound used in the compositions and methods of the present invention comprises an amine functional group, a prodrug can be formed by the replacement of a hydrogen atom in the amine group with a group such as $R^X$-carbonyl, $R^X$O-carbonyl, $NR^X R^{X\prime}$-carbonyl where $R^X$ and $R^{X\prime}$ are each independently ($C_1$-$C_{10}$)alkyl, ($C_3$-$C_7$)cycloalkyl, benzyl, or $R^X$-carbonyl is a natural α-aminoacyl or natural α-aminoacyl-natural α-aminoacyl, —C(OH)C(O)$OY^X$ wherein $Y^X$ is H, ($C_1$-$C_6$)alkyl or benzyl), —C($OY^{X0}$)$Y^{X1}$ wherein $Y^{X0}$ is ($C_1$-$C_4$) alkyl and $Y^{X1}$ is ($C_1$-$C_6$)alkyl, carboxy($C_1$-$C_6$)alkyl, amino($C_1$-$C_4$)alkyl or mono-N- or di-N,N—($C_1$-$C_6$)alkylaminoalkyl, —C($Y^{X2}$) $Y^{X3}$ wherein $Y^{X2}$ is H or methyl and $Y^{X3}$ is mono-N- or di-N,N—($C_1$-$C_6$)alkylamino, morpholino, piperidin-1-yl or pyrrolidin-1-yl.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol). A particular embodiment of a pharmaceutically acceptable salt of tafamidis used in the combinations and methods of the present invention is tafamidis meglumine.

It will be recognized that the compounds used in the compositions and methods of this invention can exist in radio labelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3$H, $^{14}$C, $^{32}$P, $^{35}$S, $^{18}$F and $^{36}$Cl, respectively. Compounds used in the compositions and methods of this invention which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability. Radio labelled compounds of this invention can generally be prepared by methods well known to those skilled in the art. Conveniently, such radio labelled compounds can be prepared by carrying out the procedures disclosed herein except substituting a readily available radio labelled reagent for a non-radio labelled reagent.

It will be recognized by persons of ordinary skill in the art that some of the compounds used in the compositions and methods of this invention may have at least one asymmetric carbon atom and therefore there are enantiomers or diastereomers. Diasteromeric mixtures can be separated into their individual diastereomers on the basis of their physicochemical differences by methods known per se as, for example, chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing, including both chemical hydrolysis methods and microbial lipase hydrolysis methods, e.g., enzyme catalyzed hydrolysis) the individual diastereomers to the corresponding pure enantiomers. All such isomers, including diastereomers, enantiomers and mixtures thereof are considered as part of this invention. Also, some of the compounds used in the compositions and methods of this invention are atropisomers (e.g., substituted biaryls) and are considered as part of this invention.

In addition, when the compound 2-(3,5-dichlorophenyl)-1,3-benzoxazole-6-carboxylic acid or a pharmaceutically acceptable salt or prodrug thereof or the additional therapeutic agents, form hydrates or solvates, they are also within the scope of the invention.

Administration of the compounds used in the compositions and methods of this invention can be via any method that delivers a compound of this invention systemically and/or locally. These methods include oral, parenteral, and intraduodenal routes, etc. The compounds of this invention are administered orally, but parenteral administration (e.g., intravenous, intramuscular, transdermal, subcutaneous, rectal or intramedullary) may also be utilized, for example, where oral administration is inappropriate for the target or where the patient is unable to ingest the drug. The compounds used in the compositions and methods of this invention may also be applied locally to a site in or on a patient in a suitable carrier or diluent.

In general an effective dosage for 2-(3,5-dichlorophenyl)-1,3-benzoxazole-6-carboxylic acid or a pharmaceutically acceptable salt thereof, used in the pharmaceutical compositions and methods of this invention is in the range of 0.001 to 100 mg/kg/day, preferably a dose of 10 mg/day to 100 mg/day administered as a single dose.

The amount and timing of administration will, of course, be dependent on the subject being treated, on the severity of the affliction, on the manner of administration and on the judgment of the prescribing physician. Thus, because of patient to patient variability, the dosages given herein are guidelines and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases. The dose may be given once a day or more than once a day and may be given in a sustained release or controlled release formulation. It is also possible to administer the compounds using a combination of an immediate release and a controlled release and/or sustained release formulation.

The administration of 2-(3,5-dichlorophenyl)-1,3-benzoxazole-6-carboxylic acid or a pharmaceutically acceptable salt or prodrug thereof and an additional therapeutic agent or the combination thereof can be according to any continuous or intermittent dosing schedule. Once a day, multiple times a day, once a week, multiple times a week, once every two weeks, multiple times every two weeks, once a month, multiple times a month, once every two months, once every three months, once every six months and once a year dosing are non-limiting examples of dosing schedules for 2-(3,5-dichlorophenyl)-1,3-benzoxazole-6-carboxylic acid or a pharmaceutically acceptable salt or prodrug thereof and an additional therapeutic agent or the combination thereof.

The compounds used in the compositions and methods of the present invention are generally administered in the form of a pharmaceutical composition comprising at least one of the compounds together with a pharmaceutically acceptable vehicle or diluent. Thus, the compounds used in the compositions and methods of this invention can be administered in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof. Acceptable dosage forms for 2-(3,5-dichlorophenyl)-1,3-benzoxazole-6-carboxylic acid or a pharmaceutically acceptable salt or prodrug thereof and an additional therapeutic agent include tablets, capsules, solutions and suspensions. Other suitable formulations will be apparent to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995). The pharmaceutical combinations of this invention generally will be administered in a convenient formulation. The following formulation examples only are illustrative and are not intended to limit the scope of the present invention.

In the formulations that follow, "active ingredient" means tafamidis or a pharmaceutically acceptable salt or prodrug thereof, or an additional therapeutic agent or a combination of a first compound, tafamidis or a pharmaceutically acceptable salt or prodrug thereof in combination with a therapeutically effective amount of one or more additional therapeutic agents. In a preferred embodiment, the first compound of the "active ingredient" used in the formulation is tafamidis free acid or tafamidis meglumine salt. A preferred dosage of tafamidis meglumine salt in certain of the formulations is selected from 20 mg, 40 mg, 60 mg or 80 mg and a preferred dosage of tafamidis free acid in certain of the formulations is selected from 15.25 mg, 30.5 mg, 45.75 mg and 61 mg.

| Ingredient | Quantity (mg/capsule) |
|---|---|
| Formulation 1: Gelatin Capsules | |
| Hard gelatin capsules are prepared using the following: | |
| Active ingredient | 0.25-400 |
| Starch, NF | 0-650 |
| Starch flowable powder | 0-50 |
| Silicone fluid 350 centistokes | 0-15 |
| A tablet formulation is prepared using | |
| the ingredients below: Formulation 2: Tablets | |
| Active ingredient | 0.25-400 |
| Cellulose, microcrystalline | 200-650 |
| Silicon dioxide, fumed | 10-650 |
| Stearate acid | 5-15 |

The components are blended and compressed to form tablets.

Alternatively, tablets each containing 0.25-400 mg of active ingredients are made up as follows:

| Formulation 3: Tablets | |
|---|---|
| Ingredient | Quantity (mg/tablet) |
| Active ingredient | 0.25-400 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25-100 mg of active ingredient per 5 ml dose are made as follows:

| Formulation 4: Suspensions | |
| --- | --- |
| Ingredient | Quantity (mg/5 ml) |
| Active ingredient | 0.25-100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
| --- | --- |
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
| --- | --- |
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
| --- | --- |
| Ingredient | Quantity |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

| Formulation 8: Soft Gelatin Capsule with Oil Formulation | |
| --- | --- |
| Ingredient | Quantity (mg/capsule) |
| Active ingredient | 10-500 |
| Olive Oil or Miglyol ® Oil | 500-1000 |

Formulation 9: Intravenous Formulation of Tafamidis Meglumine and Patisiran Sodium 20 mg tafamidis meglumine, 10.5 mg of patisiran sodium (equivalent 10 mg of patisiran), 62 mg cholesterol USP, 130 mg (6Z,9Z,28Z,31Z)-heptatriaconta-6,9,28,31tetraen-19-yl-4-(dimethylamino) butanoate (DLin-MC3-DMA), 33 mg 1,2-distearoyl-sn-glycero-3-phosphocholine (DSPC), 16 mg α-(3'-{[1,2-di(myristyloxy)propanoxy]carbonylamino}propyl)-ω-methoxy, polyoxyethylene (PEG2000C-DMG), 2.0 mg potassium phosphate monobasic anhydrous NF, 88 mg sodium chloride USP, 23 mg sodium phosphate dibasic heptahydrate USP, and 10 mL Water for Injection USP and the total solution pH is ~7.0

Formulation 10: Intravenous Formulation of Tafamidis Meglumine and Patisiran Sodium 40 mg tafamidis meglumine, 10.5 mg of patisiran sodium (equivalent 10 mg of patisiran), 62 mg cholesterol USP, 130 mg (6Z,9Z,28Z,31Z)-heptatriaconta-6,9,28,31tetraen-19-yl-4-(dimethylamino) butanoate (DLin-MC3-DMA), 33 mg 1,2-distearoyl-sn-glycero-3-phosphocholine (DSPC), 16 mg α-(3'-{[1,2-di(myristyloxy)propanoxy]carbonylamino}propyl)-ω-methoxy, polyoxyethylene (PEG2000C-DMG), 2.0 mg potassium phosphate monobasic anhydrous NF, 88 mg sodium chloride USP, 23 mg sodium phosphate dibasic heptahydrate USP, and 10 mL Water for Injection USP and the total solution pH is ~7.0

Formulation 11: Intravenous Formulation of Tafamidis Meglumine and Patisiran Sodium 60 mg tafamidis meglumine, 10.5 mg of patisiran sodium (equivalent 10 mg of patisiran), 62 mg cholesterol USP, 130 mg (6Z,9Z,28Z,31Z)-heptatriaconta-6,9,28,31tetraen-19-yl-4-(dimethylamino) butanoate (DLin-MC3-DMA), 33 mg 1,2-distearoyl-sn-glycero-3-phosphocholine (DSPC), 16 mg α-(3'-{[1,2-di(myristyloxy)propanoxy]carbonylamino}propyl)-ω-methoxy, polyoxyethylene (PEG2000C-DMG), 2.0 mg potassium phosphate monobasic anhydrous NF, 88 mg sodium chloride USP, 23 mg sodium phosphate dibasic heptahydrate USP, and 10 mL Water for Injection USP and the total solution pH is ~7.0

Formulation 12: Intravenous Formulation of Tafamidis Meglumine and Patisiran Sodium 80 mg tafamidis meglumine, 10.5 mg of patisiran sodium (equivalent 10 mg of patisiran), 62 mg cholesterol USP, 130 mg (6Z,9Z,28Z,31Z)-heptatriaconta-6,9,28,31tetraen-19-yl-4-(dimethylamino) butanoate (DLin-MC3-DMA), 33 mg 1,2-distearoyl-sn-glycero-3-phosphocholine (DSPC), 16 mg α-(3'-{[1,2-di(myristyloxy)propanoxy]carbonylamino}propyl)-ω-methoxy, polyoxyethylene (PEG2000C-DMG), 2.0 mg potassium phosphate monobasic anhydrous NF, 88 mg sodium chloride USP, 23 mg sodium phosphate dibasic heptahydrate USP, and 10 mL Water for Injection USP and the total solution pH is ~7.0

Formulation 13: Intravenous Formulation of Tafamidis Meglumine and Patisiran Sodium 100 mg tafamidis meglumine, 10.5 mg of patisiran sodium (equivalent 10 mg of patisiran), 62 mg cholesterol USP, 130 mg (6Z,9Z,28Z,31Z)-heptatriaconta-6,9,28,31tetraen-19-yl-4-(dimethylamino) butanoate (DLin-MC3-DMA), 33 mg 1,2-distearoyl-sn-glycero-3-phosphocholine (DSPC), 16 mg α-(3'-{[1,2-di(myristyloxy)propanoxy]carbonylamino}propyl)-ω-methoxy, polyoxyethylene (PEG2000C-DMG), 2.0 mg potassium phosphate monobasic anhydrous NF, 88 mg sodium chloride USP, 23 mg sodium phosphate dibasic heptahydrate USP, and 15 mL Water for Injection USP and the total solution pH is ~7.0

Formulation 14: Subcutaneous Formulation of Tafamidis Meglumine and Inotersen Sodium 20 mg tafamidis meglumine, 300 mg inotersen sodium (equivalent 284 mg inotersen), 3 mL Water for Injection USP and pH is ~7.5 (adjusted with 1 M HCl and/or 1 M NaOH as necessary for pH control).

Formulation 15: Subcutaneous Formulation of Tafamidis Meglumine and Inotersen Sodium 10 mg tafamidis meglumine, 300 mg inotersen sodium (equivalent 284 mg inotersen), 1.5 mL Water for Injection USP and pH is ~7.5 (adjusted with 1 M HCl and/or 1 M NaOH as necessary for pH control).

Formulations 16-18: Sachet of Tafamidis Meglumine and Ataluren for Oral Administration 20 mg of tafamidis meglumine in admixture with 125 mg, 250 mg or 1000 mg ataluren in a sachet.

Formulations 19-21: Sachet of Tafamidis Meglumine and Ataluren for Oral Administration 5 mg of tafamidis meglumine in admixture with 125 mg, 250 mg or 1000 mg ataluren in a sachet.

Another aspect of the present invention is a kit comprising:
  a. an amount of tafamidis or a pharmaceutically acceptable salt or prodrug thereof, and a pharmaceutically acceptable carrier or diluent in a first unit dosage form;
  b. an amount of a second therapeutic agent, and a pharmaceutically acceptable carrier or diluent in a second unit dosage form; and
  c. a container.

The kit comprises two separate pharmaceutical compositions: tafamidis or a pharmaceutically acceptable salt or prodrug thereof and a second therapeutic agent as described above. The kit comprises container means for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc. . . . Second Week, Monday, Tuesday . . . " etc. Other variations of memory aids will be readily apparent. A "daily dose" can be a single tablet or capsule or several tablets or capsules to be taken on a given day. Also, a daily dose of tafamidis or a pharmaceutically acceptable salt or prodrug thereof can consist of one tablet or capsule while a daily dose of the additional therapeutic agent can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter that indicates the number of daily doses that have been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The tafamidis or a pharmaceutically acceptable salt or prodrug thereof and the additional therapeutic agent can be administered in the same dosage form or in different dosage forms at the same time or at different times. All variations of administration methods are contemplated. A preferred method of administration is to administer the combination in the same dosage form at the same time. For example, tafamidis or a pharmaceutically acceptable salt or prodrug thereof can be taken parenterally in the same dosage form as an additional therapeutic agent, such as a siRNA or antisense oligonucleotide. Another preferred administration method is to administer the tafamidis or a pharmaceutically acceptable salt or prodrug thereof in one dosage form and the additional therapeutic agent in another, both of which are taken at the same time. For example, tafamidis or a pharmaceutically acceptable salt or prodrug thereof can be taken orally and an additional therapeutic agent such as a siRNA therapeutic agent or antisense oligonucleotide can be administered parenterally, such as intravenously or subcutaneously. A preferred embodiment of the present invention is a method of treating TTR amyloidosis by administering tafamidis or a pharmaceutically acceptable salt or prodrug thereof parenterally in the same dosage form as an additional therapeutic agent, such as a siRNA or antisense oligonucleotide on one day, followed by once daily oral administration of tafamidis or a pharmaceutically acceptable salt or prodrug thereof for a period of time until the next parenteral administration of tafamidis with the additional therapeutic agent in the single dosage form.

The tafamidis or a pharmaceutically acceptable salt or prodrug thereof used in the compositions and methods of this invention are all adapted to therapeutic use as agents that stabilize transthyretin in mammals, particularly humans. The additional therapeutic agents used in the compositions and methods of this invention are all adapted to therapeutic use as agents that are useful for the treatment of a transthyretin amyloidosis, such as transthyretin polyneuropathy or transthyretin cardiomyopathy. By virtue of these activities, the combinations of this invention are useful for treating familial amyloidotic polyneuropathy (FAP) or familial amyloidotic cardiomyopathy (FAC), as used herein means that a patient having familial amyloidotic polyneuropathy (FAP) or familial amyloidotic cardiomyopathy (FAC) or for treating patients at risk of having familial amyloidotic polyneuropathy (FAP) or familial amyloidotic cardiomyopathy (FAC). The combinations of this invention are particularly advantageous and provide synergistic activity in the treatment of transthyretin cardiomyopathy and/or transthyretin polyneuropathy.

The utility of the compositions of the invention and the salts thereof as medical agents in the treatment of the above described disease/conditions in mammals (e.g., humans, male or female) is demonstrated by the activity of the combinations of this invention in conventional assays and the in vitro and in vivo assays described below. The in vitro and in vivo assays (with appropriate modifications within the skill in the art) may be used to determine the activity of analogous agents as well as the combinations of this invention. Such assays also provide a means whereby the activities of the compositions of this invention can be compared with the activities of other known compounds. The results of these comparisons are useful for determining dosage levels in mammals, including humans, for the treatment of such diseases.

The following protocols can be varied when appropriate by those skilled in the art.

Methods

There are a number of published and well established in vitro assays that are used to evaluate the ability of test compounds to stabilize the TTR tetramers or prevent TTR dissociation, proteolysis, misfolding, aggregation or fibril formation. Examples include, but are not limited to, fluorescence polarization assay, fluorescent probe binding assay, isothermal titration calorimetry assay, fibril formation assay, determination of the three-dimensional structure of ligand bound to TTR using X-ray crystallography, FRET, kinetics of transthyretin tetramer dissociation or fibril formations, immunoblots to evaluate the stabilizing effect and selectivity of compound binding to TTR in serum.

Provided herein are methods for using the disclosed combinations to increase the stability of TTR thereby preventing it from misfolding and forming TTR amyloid fibrils.

The combinations disclosed herein may be used to decrease TTR amyloid formation and/or to decrease cell dysfunction and/or death associated with TTR amyloid formation. The combinations may be used to decrease TTR amyloid formation in vitro in a cell-free system, in vitro-intra- or extra-cellularily in cell culture, and in vivo, such as TTR found in bodily fluids including but not restricted to blood, serum, cerebrospinal fluid, tissue and organs including but not restricted to the heart, the kidney, peripheral nerves, meninges, the central nervous system, the eye (including the retina and vitreous fluid) of a subject. As such, methods for using the disclosed combinations include administering the disclosed compounds in vitro, ex vivo or to a subject in vivo to increase the stability of TTR found in bodily fluids including but not restricted to blood, serum, cerebrospinal fluid, tissues and organs including but not restricted to the heart, the kidney, peripheral nerves, meninges, the central nervous system, the eyes.

Amyloid fibril formation may be determined using a turbidity assay in vitro in a cell-free system. The turbidity assay can use a wild-type TTR or a mutant of TTR with an increased tendency to form amyloid fibrils. When a wild-type TTR is used TTR amyloidogenesis may be initiated by acidification of TTR or the addition of urea. When a mutant of TTR with an increased tendency to form amyloid fibrils, acidification of TTR or addition of urea may also be used.

Also provided are methods for the stabilization of transthyretin in a tissue or in a biological fluid, and thereby inhibiting dissociation and/or misfolding. Generally, the method comprises administering to the tissue or biological fluid a composition comprising a stabilizing amount of a compound described herein that binds to transthyretin and prevents dissociation of the transthyretin tetramer by kinetic stabilization of the native state of the transthyretin tetramer. As such, methods for using the disclosed compounds include administering to the tissue or biological fluid a composition comprising a stabilizing amount of a compound described herein that binds to transthyretin and prevents dissociation of the transthyretin tetramer by kinetic stabilization of the native state of the transthyretin tetramer of TTR found in the blood, serum, cerebrospinal fluid, fluids of the central nervous system, retina and the eyes. Generally, the method involves administering to the tissue or biological fluid a stabilizing amount of a compound provided herein that binds to TTR and prevents dissociation of the TTR tetramer by kinetic stabilization of the native state of the TTR tetramer.

Thus, methods which stabilize TTR in a diseased tissue ameliorate misfolding and lessen symptoms of an associated disease and, depending upon the disease, can contribute to cure of the disease. Also contemplated herein is inhibition of TTR misfolding in a tissue. The extent of misfolding, and therefore the extent of inhibition achieved by the present methods, can be evaluated by a variety of methods, such as those described in the in PCT patent application publication no. WO 2004/056315 which is incorporated herein by reference in its entirety.

Thus, methods, which stabilize transthyretin in a diseased tissue ameliorate misfolding and lessen symptoms of an associated disease and, depending upon the disease, can contribute to cure of the disease. The target disease of methods of the present disclosure may vary and may include those diseases which result from protein misfolding (e.g., TTR folding) or diseases associated with an increased tendency to form amyloid fibrils found in the bodily fluids such as blood, serum, cerebrospinal fluid, fluids of the central nervous system and eyes. The extent of misfolding, and therefore the extent of inhibition achieved by the present methods, can be evaluated by a variety of methods.

Accordingly, in another aspect the invention includes a method of treating a TTR amyloid disease, the method comprising administering to a subject diagnosed as having a TTR amyloid disease a therapeutically effective amount of a compound that stabilizes the native state of the TTR tetramer.

In one embodiment, the invention features a method of treating a TTR amyloid disease, the method comprising administering to a subject diagnosed as having a TTR amyloid disease a therapeutically effective amount of a compound disclosed above that stabilizes TTR tetramer.

The TTR amyloid disease can be, for example, familial amyloid polyneuropathy, familial amyloid cardiomyopathy, senile systemic amyloidosis, central amyloidosis or ocular amyloidosis.

The subject treated in the present methods can be a human subject, although it is to be understood that the principles of the invention indicate that the invention is effective with respect to all mammals.

Evaluation of the Activity of the Compounds

A number of in vitro tests can be used to evaluate the therapeutic combinations for their ability to stabilize TTR tetramers or prevent dissociation, proteolysis, and formation of fibrils. The tests can include a fibril formation assay, a plasma selectivity assay, determination of the three-dimensional structure of a TTR:compound complex (e.g., by X-ray crystallography), kinetics of TTR tetramer dissociation or fibril formations, and determining the stoichiometry and energetics of TTR: compound interactions, by, for example, centrifugation or calorimetry.

The TTR that can be used in the screening methods can be wild type TTR or a mutant TTR, such as a naturally occurring mutant TTR causally associated with the incidence of a TTR amyloid disease such as familial amyloid polyneuropathy or familial amyloid cardiomyopathy. Examples of naturally occurring mutant TTRs include, but are not limited to, V122I, V30M, LSSP (the mutant nomenclature describes the substitution at a recited amino acid position, relative to the wild type, see, e.g., Saraiva et al. Hum. Mut. 17:493-503(2001)).

Isothermal Titration Calorimetry (ITC)

Calorimetric titrations can be carried out on a VP-ITC calorimeter (MicroCal, Northhampton, MA). A solution of test compound (such as tafamidis in combination with an additional agent) (25 µM in PBS pH 7.4, 100 mM KCl, 1 mM EDTA, 8% DMSO) can be prepared and titrated into an ITC cell containing 2 µM of TTR in an identical buffer. Prior to each titration, all samples are degassed for 10 minutes. 37 injections of test compounds (8.0 pL each) are injected into the ITC cell (at 25 C) to the point that TTR is fully saturated with ligand.

Integration of the thermogram after the subtraction of blanks can yield a binding isotherm and can be compared to best fit models. The data can be fit by a non-linear least squares approach with four adjustable parameters: Edt, AHI, Edq, and AH2 using the ITC data analysis module in MicroCal ORIGIN 5.0 software.

Fluorescence Polarization Binding Assays

Determination of FP probe displacement by TTR ligands. The affinity of test compounds to TTR can be determined by their ability to displace FP probe form TTR using an assay such as the one described in Alhamadsheh et al. Science Translational Medicine, 24 Aug. 2011, Vol. 3, Issue 97, pp 97ra81. In a black 384-well plates (EkK Scientific, $^1$EK-31076), FP-probe 5 (200 nM) is incubated with TTR (400 nM) in assay buffer (PBS pH 7.4, 0.01% Triton-X100, 1% DMSO in 25 pL final volumes) at room temperature. Test compounds (tafamidis in combination with an additional agent) are then added to the wells at a single concentration of 10 µM. The samples are allowed to equilibrate by agitating for 30 min at room temperature and fluorescence polarization (excitation X 485 nm, emission X 525 nm, cutoff X 515 nm) measurements are taken using a SpectraMax M5 Microplate Reader (Molecular Devices). The data are fit to the following equation $[y=(AD)/(1+(x/C)~B)+D]$ where A=maximum FP signal, B=slope, C=apparent binding constant (Kapp), and D=minimum FP signal. The apparent binding constant is reported as the mean for triplicate experiments and the best data fit is determined by R value.

Serum TTR Selectivity Assay

The binding affinity and selectivity of the of test compounds to TTR is determined by their ability to compete for covalent probe 6 binding to TTR in human serum as previously reported by Choi et al., Bioorg Med Chem. 2011, 19(4), 1505-1514.

An aliquot of 98 pL of human serum (Sigma-Aldrich) was mixed with 1 pL of test compounds (1 mM stock solution in DMSO, final concentration: 10 pM) and 1 pL of covalent probe 6 (0.36 mM stock solution in DMSO: final concentration: 3.6 pM). The fluorescence changes (~, =328 nm and g=384 nm) are monitored every 10 min using a microplate spectrophotometer reader (Molecular Devices SpectraMax MS) for 6 h at 25 C.

Measurement of Serum WT-TTR Tetramer Stability Against Acid Denaturation

All compounds are 10 mM stock solutions in DMSO and diluted accordingly with DMSO for different assays. 0.5 pi of each compound is added to 24.5 pi of human serum (from human male AB plasma, Sigma) to make the final concentration of 10 pM. The samples are incubated at 37 C for 2 h, and then 10 pi of the samples were diluted 1:10 with acidification buffer (pH 4.0, 100 mM sodium acetate, 100 mM KCl, 1 mM EDTA, 1 mM DTT). The samples for 0 hours are directly cross-linked with glutaraldehyde (final concentration of 2.5%) for 5 min, and then quenched with 10 pi of 7% sodium borohydride solution in 0.1 M NaOH; while the samples in acidification buffer are incubated at room temperature for 72 h and then cross-linked and quenched with the same protocol. All the samples are denatured with adding 100 pi SDS gel loading buffer and boiled for 5 min. 12.5 pi of each sample was separated in 12% SDS-PAGE gels and analyzed by immunoblotting using anti-TTR antiserum (DAKO A0002). The normalization is done by dividing each value of the TTR tetramer band intensity by the average of all the values at time 0.

Measurement of Serum V122I-TTR Tetramer Stability Against Acid

Subjects: Samples are obtained from patients with the V122I TTR mutation. (mutation can be confirmed by sequencing/test: 'Amyloidosis DNA titer'): The western blot analysis is performed as described above for wild type TTR. All the value of the TTR tetramer band intensity is normalized by the DMSO treated sample at time 0 which was set as 1.

Cleavage and fibrillogenesis of amyloidogenic TTR variants and wild-type TTR Proteolysis experiments can be carried out as described by Marcoux, J.; Bellotti, V. et. al. A novel mechano-enzymatic cleavage mechanism underlies transthyretin amyloidogenesis EMBO Molecular Medicine, Aug. 18, 2015, 1-13.

Fibrillogenesis of L55P, V122I, V30M, and wild-type alongside S52P and the non-amyloidogenic T119M TTR variant is carried out in glass vials stirred at 1,500 rpm (IKA magnetic stirrer) and 37° C. using 18 µM TTR in PBS pH 7.4 in the presence and in the absence of trypsin (5 ng/µl). The glass vial has an air/water interface of 1.5 $cm^2$. Turbidity at 400 nm is monitored over time until it reaches a plateau (72 h). Samples are analyzed by SDS-homogeneous 15% PAGE (GE Healthcare) under reducing conditions, and bands corresponding to the intact TTR protomer are quantified with Quantity One software (Bio-Rad). After staining with alcoholic acid Congo red (CR), aggregated material is observed with polarized light microscopy. Morphology of wild-type TTR aggregates is characterized by electron microscopy as previously described (Mangione, P. P. et al, Proteolytic cleavage of Ser52Pro variant transthyretin triggers its amyloid fibrillogenesis, Proc Natl Acad Sci USA 2014, 111, 1539-1544). Fibrillogenesis of V122I TTR is monitored by light scattering at 400 nm in the presence and the absence of 0.5-, one-, two- and fourfold molar excess of tafamidis (Bulawa, C. E. et al, Tafamidis, a potent and selective transthyretin kinetic stabilizer that inhibits amyloid cascade, Proc Natl Acad Sci USA 2012, 109, 9629-9634), and in the presence of tafamidis in combination with another therapeutic agent, such as another TTR stabilizer including compounds such as diflunisal (Berk, J. L. et al, Repurposing diflunisal for familial amyloid polyneuropathy: a randomized clinical trial, JAMA 2013, 310, 2658-2667), mds84 (Kolstoe, S. E. et al, Trapping of palindromic ligands with native transthyretin prevents amyloid formation, Proc Natl Acad Sci USA 2010, 107, 20483-20488) and AG10 or analogues thereof.

The effect of tafamidis both alone and in combination with other therapeutic agents on V30M TTR fibril formation is also monitored as described above. For all the ligand inhibition experiments, the time of incubation of TTR with trypsin at 37° C. was extended to 96 h. The ThT assay could not be used because mds84 strongly interferes with the fluorescence measurement. Quantification of the band of the full-length protomers in SDS-PAGE is performed as measurement of the susceptibility to proteolysis of TTR as described above. Experimental data are fitted to nonlinear regression curves using GraphPad Prism v5. Concentrations of ligand-inhibiting TTR fibril formation by 50% (IC50) are determined from aggregation curves and expressed as mean_SD of three independent experiments.

Subunit exchange can be carried out as described in Wiseman, R. L., N. S. Green, and J. W. Kelly, Kinetic stabilization of an oligomeric protein under physiological conditions demonstrated by a lack of subunit exchange: implications for transthyretin amyloidosis Biochemistry 2005, 44(25), 9265-9274.

Expression and Purification of Wild-Type TTR and Flag-Tag Wild-Type TTR Both wild-type TTR and flag-tag wild-type TTR were prepared as previously described (See Schneider, F., Hammarstrom, P., and Kelly, J. W. Transthyretin slowly exchanges subunits under physiological conditions: A convenient chromatographic method to study subunit exchange in oligomeric proteins, Protein Sci. 2001, 10, 1606-1613 and Lashuel, H. A., Wurth, C., Woo, L., and Kelly, J. W. The most pathogenic transthyretin variant, L55P, forms amyloid fibrils under acidic conditions and protofilaments under physiological conditions, Biochemistry 1999, 38, 13560-13573).

Briefly, both wild-type and flag-tag wild-type TTR are expressed in BL21 *Escherichia coli*. Selection is performed in Luria-Bertani broth with 100 μg/mL ampicillin (wild-type TTR) or 150 μg/mL kanamycin (flag-tag wild-type TTR). 1 mM IPTG is added to the cells when an $OD_{600nm}$ of 0.8-1.0 was achieved. Cells are lysed with three rounds of sonication at 4° C., and the supernatant is collected following centrifugation. The supernatant is then treated with a 50% ammonium sulfate and then collected following centrifugation. TTR is precipitated by centrifugation following a 50-90% ammonium sulfate treatment. The protein is then dialyzed overnight into 25 mM Tris pH 8.0, 1 mM EDTA with 7000 MW dialysis tubing (Snakeskin from Pierce Biomedical). TTR is purified first on a Source15Q anion exchange column (Amersham Biosciences) eluting with either a 200-350 mM NaCl gradient (wild-type TTR) or a 200-500 mM NaCl gradient (flag-tag wild-type TTR) at 4° C. The TTR is further purified by gel filtration chromatography using a Superdex 75 column (Amersham Biosciences; 50 mM sodium phosphate pH 7.2, 100 mM KCl, 1 mM EDTA). The protein is identified by LC-MS analysis (Hewlitt-Packard 1100-MSD mass spectrometer; wild-type TTR-13890; flag-tag wild-type TTR-15880).

Subunit Exchange of Wild-Type TTR and Flag-Tag Wild-Type TTR

Homotetrameric wild-type TTR and homotetrameric flag-tag wild-type TTR are prepared at the desired concentrations (0.1, 1, or 20 μM; 50 mM sodium phosphate pH 7.2, 100 mM KCl, 1 mM EDTA). The proteins are mixed in equal volumes into an eppendorf tube and incubated at 25° C. for the indicated times. Subunit exchange is followed using a SMART system equipped with a μPeak monitor and a Mono Q PC 1.6/5 column, as previously described. A total of 50 μL of the exchange reaction is added to the SMART system running a gradient of 240-420 mM NaCl in 25 mM Tris pH 8.0, 1 mM EDTA. Because the flag-tag provides ~6 negative charges to each tagged TTR subunit (pH 7), the more flag-tag TTR subunits in the tetramer the longer the retention time on the anion exchange column. Integration of the observed UV curves is performed using SMART Manager 1.41 software according to the manager's instructions. The extent of exchange is calculated by dividing the integration of the specific tetramer by the total integration determined for all of the tetramers. The fraction exchange is calculated using the predicted statistical distribution of the various stoichiometries at the end of the exchange reaction (tetramers 1 and 5: [1−(extent of exchange−0.0625)/(0.50−0.0625)]; tetramers 2 and 4: [extent of exchange/0.25]; tetramer 3: [(extent of exchange)/0.375]). The reported rate constants of exchange are determined from plotting the fraction exchange data in Kaleidograph and fitting the results to a first-order single-exponential kinetic equation.

Inhibition of Subunit Exchange with Tafamidis in Combination with Additional Therapeutic Agents Tafamidis, either alone or in combination with additional therapeutic agent(s) are added to both homotetrameric TTR solutions (wild-type TTR and flag-tag wild-type TTR) at the indicated concentrations from a 1 mM solution of either tafamidis alone or the combination or tafamidis and additional therapeutic agent in DMSO. The homotetrameric solutions were then mixed to commence subunit exchange and analyzed as above.

WT and V122I TTR Fibril Formation Inhibition Assay

Figure 1:
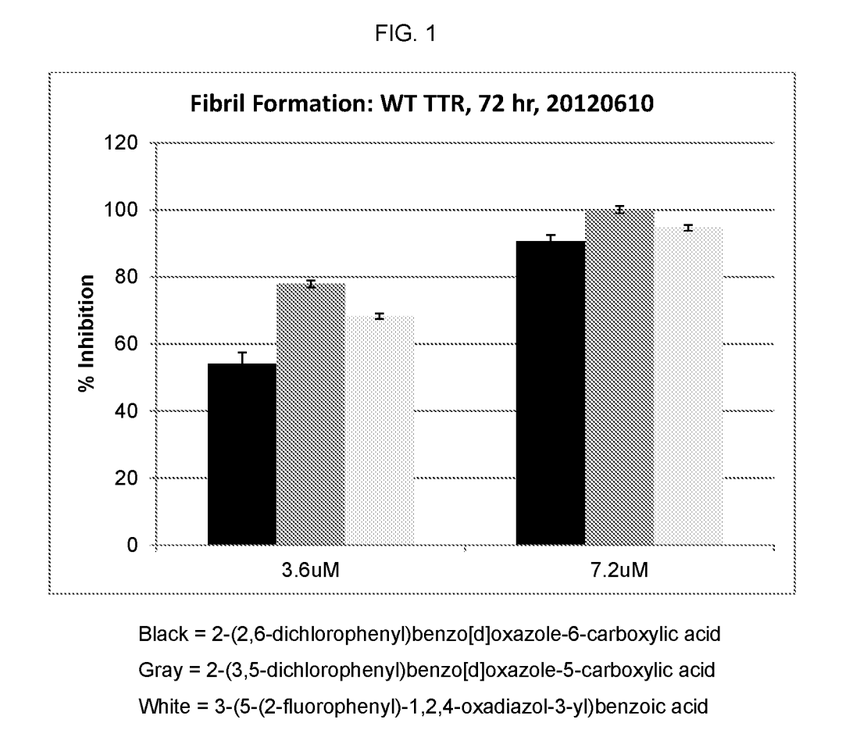
FIG. 1 depicts the percentage inhibition of wild type transthyretin fibril formation by 2-(2,6-dichlorophenyl)benzo[d]oxazole-6-carboxylic acid; 2-(3,5-dichlorophenyl)benzo[d]oxazole-5-carboxylic acid and 3-(5-(2-fluorophenyl)-1,2,4-oxadiazol-3-yl)benzoic acid (ataluren); each at a concentration of 3.6 µM or 7.2 µM.
Figure 2:
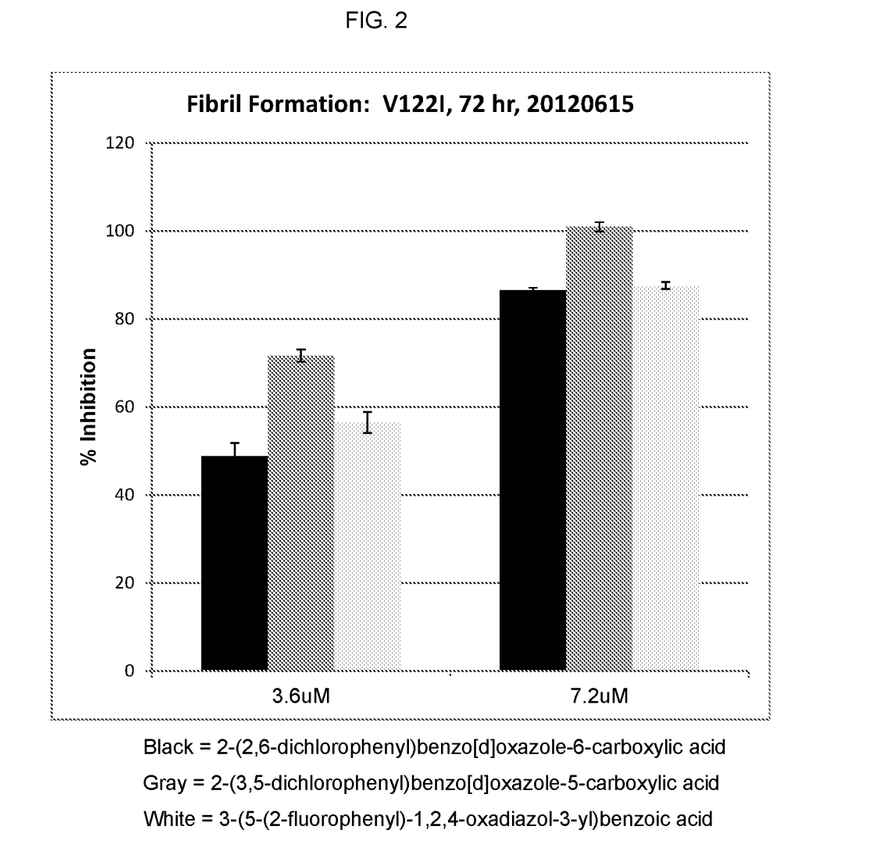
FIG. 2 depicts the percentage inhibition of V122I transthyretin fibril formation by 2-(2,6-dichlorophenyl)benzo[d]oxazole-6-carboxylic acid; 2-(3,5-dichlorophenyl) benzo[d]oxazole-5-carboxylic acid and 3-(5-(2-fluorophenyl)-1,2,4-oxadiazol-3-yl)benzoic acid (ataluren); each at a concentration of 3.6 µM or 7.2 µM.

Inhibition of WT and V122I TTR fibril formation under acidic conditions after 72 h-a sufficient period for aggregation to go to completion in the vehicle control (See Hurshman, A. R., White, J. T., Powers, E. T., Kelly, J. W.; Transthyretin aggregation under partially denaturing conditions is a downhill polymerization. *Biochemistry* 2004, 43, 7365-7381). Purified TTR tetramers (WT or V122I at 3.6 μM) were mixed with DMSO (vehicle control), Fx-1005 (positive control, See Razavi H, et al. Benzoxazoles as transthyretin amyloid fibril inhibitors: synthesis, evaluation, and mechanism of action. *Angew Chem Int Ed Engl* 2003, 42, 2758-2761), Fx-1003 (positive control) or PTC124 at final concentrations of 3.6 and 7.2 μM, and incubated for 30 minutes at 25° C. After adjusting the pH to 4.4 or 4.5, samples were incubated at 37° C. for 72 h. The turbidity was then measured at 350 nm using a UV-vis spectrometer. All endpoint amyloid fibril formation yields (which are slightly different for WT and V122I) were normalized for each allele to amyloidogenesis in the absence of stabilizer, assigned to be 100% fibril formation. Therefore, 5% fibril formation corresponds to a compound inhibiting 95% of TTR fibril formation after 72 h (See Miroy, G. J., et al. Inhibiting transthyretin amyloid fibril formation via protein stabilization. *Proc Natl Acad Sci USA* 1996, 93, 15051-15056). Error bars represent the minimum and maximum values from three technical replicates. Measurements for V122I were performed at pH 4.5 because this allele demonstrates a similar rate of fibril formation at a pH of 4.5 as observed for WT and V30M at a pH of 4.4. Thus, stabilization was tested under conditions of comparable kinetics of fibril formation for the three alleles, thus the kinetics of aggregation have a small role relative to the fraction free tetramer which dominates the amount of TTR aggregates at the endpoint (72 h).

The therapeutic combinations and methods of the present invention can be evaluated for efficacy in treating TTR amyloidosis in patients by assessing clinically relevant measures such as the change in mNIS+7 score from baseline, Norfolk QOL-DN, NIS-weakness, activities of daily living (R-ODS), 10-meter walk, mBMI, autonomic function, EQ-SD QOL, serum TTR level, cardiac assessments, grip strength measurement and skin biopsy for determination of nerve fiber density and presence of amyloid.

It is to be understood that the present invention provides combinations comprising the compound 2-(3,5-dichlorophenyl)-1,3-benzoxazole-6-carboxylic acid or a pharmaceutically acceptable salt or prodrug thereof, and one or more additional therapeutic agents. These combinations can be employed for specific uses as disclosed herein. For example, one such combination is 2-(3,5-Dichlorophenyl)-1,3-benzoxazole-6-carboxylic acid or a pharmaceutically acceptable salt thereof in combination with one or more additional therapeutic agents for the treatment of TTR amyloidosis. The present invention also includes the combination of 2-(3,5-dichlorophenyl)-1,3-benzoxazole-6-carboxylic acid or a pharmaceutically acceptable salt or prodrug thereof, and one or more additional therapeutic agents for the treatment of TTR amyloidosis wherein the one or more additional therapeutic agents are administered to the patient at the same time or at different times and in the same dosage form or different dosage form either together or separately. The present invention also provides for the use of 2-(3,5-dichlorophenyl)-1,3-benzoxazole-6-carboxylic acid or a pharmaceutically acceptable salt thereof in combination with one or more additional therapeutic agents for the manufacture of a medicament for the treatment of TTR amyloidosis. The present invention further provides for the use of a pharmaceutical composition comprising 2-(3,5-dichlorophenyl)-1,3-benzoxazole-6-carboxylic acid or a pharmaceutically acceptable salt thereof in combination with one or more additional therapeutic agents for the treatment of TTR amyloidosis. All specific embodiments of the present invention described herein may also be described in these alternative formats as appropriate.

All documents cited in this application, including patents and patent applications, are hereby incorporated by reference.

What is claimed is:

1. A method of treating TTR amyloidosis in a patient, the method comprising administering to a patient in need thereof a therapeutically effective amount of 2-(3,5-dichlorophenyl)-1,3-benzoxazole-6-carboxylic acid or a pharmaceutically acceptable salt thereof in combination with one or more additional therapeutic agents wherein the additional therapeutic agent is ataluren.

2. The method of claim 1 wherein ataluren is administered to the patient orally three times a day for a total dosage of approximately 40 mg/kg and tafamidis or a pharmaceutically acceptable salt thereof is administered to the patient orally once a day.

3. The method of claim 2 wherein 80 mg of tafamidis meglumine or 61 mg of tafamidis free acid is administered.

4. The method of claim 1 wherein ataluren and tafamidis meglumine or tafamidis free acid are administered to the patient together orally three times a day wherein the first and second doses comprise 10 mg/kg ataluren and either 20 mg tafamidis meglumine or 15.25 mg tafamidis free acid; and the third dose comprises either 40 mg tafamidis meglumine or 30.5 mg tafamidis free acid.

5. A method of inhibiting TTR fibril formation in a patient, the method comprising administering a therapeutically effective amount of ataluren or a pharmaceutically acceptable salt thereof to a patient.

* * * * *